(12) United States Patent
Cannell et al.

(10) Patent No.: US 7,754,194 B2
(45) Date of Patent: Jul. 13, 2010

(54) HAIR RELAXER COMPOSITIONS UTILIZING BIOACTIVE GLASS

(75) Inventors: David W. Cannell, Plainfield, NJ (US); Sawa Hashimoto, Westfield, NJ (US); Katherine Natalie Barger, Cranford, NJ (US); Nghi Van Nguyen, Edison, NJ (US)

(73) Assignee: L'Oréal (FR)

( * ) Notice: Subject to any disclaimer, the term of this patent is extended or adjusted under 35 U.S.C. 154(b) by 778 days.

(21) Appl. No.: 11/099,900

(22) Filed: Apr. 6, 2005

(65) Prior Publication Data

US 2006/0228316 A1    Oct. 12, 2006

(51) Int. Cl.
*A61K 8/18*     (2006.01)
(52) U.S. Cl. .................................................. 424/70.2
(58) Field of Classification Search ........................ None
See application file for complete search history.

(56) References Cited

U.S. PATENT DOCUMENTS

| | | | |
|---|---|---|---|
| 4,390,033 A * | 6/1983 | Khalil et al. ................. | 132/202 |
| 4,416,296 A * | 11/1983 | Meyers ......................... | 132/203 |
| 4,950,485 A * | 8/1990 | Akhtar et al. ................ | 424/70.2 |
| 5,639,449 A * | 6/1997 | Syed et al. .................. | 424/70.17 |
| 5,834,008 A | 11/1998 | Greenspan et al. | |
| 6,046,160 A | 4/2000 | Obi-Tabot | |
| 6,187,743 B1 | 2/2001 | Obi-Tabot | |
| 6,423,343 B1 | 7/2002 | Lee et al. | |
| 6,428,800 B2 | 8/2002 | Greenspan et al. | |
| 6,482,444 B1 | 11/2002 | Bellantone et al. | |
| 6,495,168 B2 | 12/2002 | West et al. | |
| 6,517,863 B1 | 2/2003 | LaTorre et al. | |
| 6,562,327 B1 | 5/2003 | Nguyen et al. | |
| 6,589,928 B1 | 7/2003 | Lee | |
| 6,663,878 B1 | 12/2003 | Greenspan et al. | |
| 6,756,060 B1 | 6/2004 | Greenspan et al. | |
| 2002/0086039 A1 | 7/2002 | Lee et al. | |
| 2004/0005284 A1 | 1/2004 | Nguyen et al. | |
| 2004/0166074 A1 | 8/2004 | Darkwa et al. | |
| 2004/0228905 A1 | 11/2004 | Greenspan et al. | |
| 2005/0009682 A1 | 1/2005 | Zimmer et al. | |

FOREIGN PATENT DOCUMENTS

| | | |
|---|---|---|
| DE | 102 41 495 | 9/2003 |
| EP | 1 364 639 | 11/2003 |
| WO | WO-01/72262 | 10/2001 |
| WO | WO-03/075869 | 9/2003 |
| WO | WO-03/082358 | 10/2003 |

OTHER PUBLICATIONS

European Search Report, EP 06 25 1948, Dated, Jul. 10, 2006.
The Science of Hair Care, edited by Charles Zviak (1986) pp. 185-187.
An Introduction to Bioceramics (Hench & Wilson eds.), World Scientific (1993).
Hawley'S Condensed Chemical Dictionary, revised by Richard J. Lewis, Sr. (12th edition 1993) p. 240 and 991.
Lee et al., "Bioactive Glasses: A Potential New Class of Active Ingredients for Personal Care Products," 129 SOFW-Journal (2003) p. 2-8.

* cited by examiner

*Primary Examiner*—Humera N Sheikh
*Assistant Examiner*—Bethany Barham
(74) *Attorney, Agent, or Firm*—Lerner, David, Littenberg, Krumholz & Mentlik, LLP

(57) ABSTRACT

A composition used for relaxing/straightening hair containing: (a) at least one hydroxide generator in an amount sufficient to relax/straighten keratin fibers; (b) at least one bioactive glass component; and (c) optionally, at least one complexing agent.

9 Claims, No Drawings

HAIR RELAXER COMPOSITIONS UTILIZING BIOACTIVE GLASS

FIELD OF THE INVENTION

The present invention relates to a composition and process for relaxing/straightening keratin fibers using a combination of at least one hydroxide generator in an amount effective to relax keratin fibers, and a bioactive glass component.

BACKGROUND OF THE INVENTION

In today's market, there is an increasing demand for the hair care products referred to as hair relaxers, which relax or straighten naturally curly or kinky hair. A hair relaxer can be a product that is applied in a hair salon by a professional or in the home by the individual consumer. One of the benefits of straightening or relaxing the curls of very curly hair is an increase in hair manageability and ease of styling.

Normally, the hair relaxing process is a chemical process which alters the chemical bonds in the hair and forms lanthionine. Hair fiber, a keratinous material, contains proteins or polypeptides, many of which are bonded together by disulfide bonds (—S—S—). A disulfide bond that is formed from the sulfhydryl groups (—SH) of two cysteine residues results in a cystine residue. While there are other types of bonds which occur between the polypeptides that make up hair, such as salt bonds, the permanent curling or the shape of the hair is essentially dependent on the disulfide bonds of cystine residues.

As a result, relaxing or straightening of hair can be achieved by disrupting the disulfide bonds of the hair fibers with an alkaline or a reducing agent. The chemical disruption of disulfide bonds by an alkaline agent is usually combined with mechanical straightening of the hair, such as combing, where straightening occurs through changing of the relative positions of opposite polypeptide chains. The reaction is subsequently terminated by rinsing and/or the application of a neutralizing composition.

The alkaline reaction is normally initiated by hydroxide ions. Not to be limited by theory, there are two reaction sequences that are predominantly used to explain the disruption of the disulfide bonds in hair by hydroxide ions, both of which result in lanthionine formation. One sequence is a bimolecular nucleophilic substitution mechanism where the hydroxide ion directly attacks the disulfide linkage, resulting in the formation of lanthionine and HOS. See Zviak, C., The Science of Hair Care, 185-186 (1986). The second is a β-elimination reaction initiated by the attack of a hydroxide ion on a hydrogen atom located on the carbon atom that is in the β-position to the disulfide bond. Id. The result is the formation of dehydroalanine, which in turn reacts with the thiol of the cysteine or the amine group of the alanine to form lanthionine and lysinoalanine. Regardless of the mechanism, the release of hydroxide ions that can penetrate the hair drives the hair relaxing process through a cystine to lanthionine transformation.

Most frequently, relaxing compositions are in the form of gels or emulsions that contain varying proportions of strong bases that are water soluble, such as sodium hydroxide, or compositions that contain slightly soluble metal hydroxides, e.g., calcium hydroxide ($Ca(OH)_2$), that are converted in situ to soluble bases, e.g., guanidine hydroxide. Traditionally, the two main technologies used in the hair care industry for generating hydroxide to relax keratin fibers are referred to as "lye," or sodium hydroxide, relaxers or "no lye" relaxers. The "lye" relaxers use sodium hydroxide in a concentration range of generally 1.5 to 2.5% (0.38-0.63 M) depending on the base or carrier used, the condition of the hair, and the speed of relaxation desired. Sodium hydroxide is extremely effective in straightening the hair but can result in a reduction in hair strength and, in some cases, partial or total loss of hair through breakage. Some manufacturers market lithium and potassium hydroxide relaxers as "no lye" but, while this is technically true, these relaxers still rely on the soluble hydroxides of the inorganic potassium or lithium.

Most other "no lye" relaxers operate by obtaining hydroxide from a slightly soluble source such as $Ca(OH)_2$. For example, the slightly soluble $Ca(OH)_2$ is mixed with guanidine carbonate to form the soluble but unstable source of hydroxide, guanidine hydroxide, and the insoluble calcium carbonate ($CaCO_3$). The reaction is driven to completion by the precipitation of $CaCO_3$ and is in effect substituting one insoluble calcium salt for another. Because guanidine hydroxide is fundamentally unstable, the components are separated until the time of use.

Guanidine carbonate and calcium hydroxide, however, create a different set of problems. The insoluble byproduct, $CaCO_3$, leaves a white residue or unattractive "whitening" or "ashing" that remains in the hair since divalent metals like calcium have a relatively good affinity to keratin. A decalcifying shampoo is subsequently needed to remove the ashing.

Thus, there is a need for a process to relax keratin fibers that has the advantages of using an insoluble metal hydroxide, such as $Ca(OH)_2$, but reduces or eliminates the problem of ashing caused by the insoluble byproduct, $CaCO_3$.

Moreover, the use of lye relaxers or no-lye relaxers may also cause irritation to the skin of a user. Thus, there is also a need to provide an effective way of relaxing/straightening keratin fibers in a manner which is less irritating to a user's skin.

SUMMARY OF THE INVENTION

To achieve these and other advantages, and in accordance with the purpose of the invention as embodied and broadly described herein, the present invention, in one aspect, provides a composition for relaxing or straightening keratin fibers comprising:
 (a) at least one hydroxide generator in an amount effective to relax keratin fibers;
 (b) a bioactive glass component; and
 (c) optionally, at least one complexing agent.

The present invention is also drawn to a process for relaxing keratin fibers comprising contacting the keratin fibers with a composition containing:
 (a) at least one hydroxide generator in an amount effective to relax the keratin fibers;
 (b) a bioactive glass component; and
 (c) optionally, at least one complexing agent.

The invention also provides for a multicomponent kit for relaxing keratin fibers, wherein the kit comprises at least two separate components. One component of the kit contains at least one hydroxide generator while the other component of the kit contains the bioactive glass component and, optionally, at least one complexing agent, in order to effectively dissociate the at least one metal hydroxide in sufficient quantity to effect relaxation of the keratin fibers in a manner which is less irritating to the user.

Additional objects and advantages of the invention will be set forth in part in the description which follows, and in part will be apparent from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention as claimed.

DETAILED DESCRIPTION OF THE INVENTION

Reference will now be made in detail to the presently preferred embodiments of the present invention. The invention, in one aspect, provides a composition for relaxing keratin fibers comprising at least one hydroxide generator, a bioactive glass and, optionally, at least one complexing agent.

Not to be limited as to theory, the relaxing of keratin fibers is driven by the release of hydroxide ions, which disrupt the disulfide bonds of cystine. The compositions of the present invention offer advantages over traditional "lye" or "no-lye" hair relaxers by providing a less irritating way of effectively relaxing and/or straightening hair.

The hydroxide generator of the present invention may be chosen from soluble metal hydroxides, slightly soluble metal hydroxides, and combinations thereof. In order to effectuate relaxation or straightening of keratin fibers, it is imperative that the composition of the present invention be capable of generating an in-use pH of at least about 11, preferably at least about 12, and more preferably at least about 13.

The at least one hydroxide generator may be chosen from monovalent metal hydroxide compounds including, but not limited to, sodium hydroxide, potassium hydroxide and lithium hydroxide, as well as multivalent metal hydroxide compounds including, but not limited to, calcium hydroxide, barium hydroxide, magnesium hydroxide, aluminum hydroxide, cupric hydroxide, strontium hydroxide, molybdenum hydroxide, manganese hydroxide, zinc hydroxide, and cobalt hydroxide.

In the event that the hydroxide generator is a monovalent metal hydroxide, it will typically be employed in an amount of from about 0.1 to about 3% by weight, preferably from about 0.2 to about 2.5% by weight, and more preferably from about 0.3 to about 2% by weight, based on the weight of the composition. However, when the hydroxide generator is a multivalent metal hydroxide, it will be employed in an amount of from about 0.1 to about 75% by weight, preferably from about 0.2 to about 50% by weight, and more preferably from about 0.3 to 20% by weight, based on the weight of the composition.

Bioactive glasses are known to those skilled in the art and are disclosed, for example, in An Introduction to Bioceramics, L. Hench and J. Wilsom, etds. World Scientific, New Jersey (1993), and in the following patent publications U.S. Pat. No. 5,834,008, WO01/72262, DE10241495, and WO03/075869 the entire contents of which are incorporated by reference. It has been surprisingly discovered that by employing a bioactive glass in combination with traditional hair relaxing systems, the degree of skin irritation experienced by the user can be reduced.

The bioactive glass of the present invention typically will contain from about 40 to about 88% by weight of silicon dioxide ($SiO_2$), up to about 35% by weight of sodium oxide ($Na_2O$), from about 4 to about 46% by weight calcium oxide (CaO) and from about 1 to about 15% by weight phosphorus oxide ($P_2O_5$). Preferably, the silicon dioxide is present in an amount of about 40 to about 68% by weight, the sodium oxide is present in an amount of about 5 to about 30% by weight, the calcium oxide is present in an amount of about 10 to about 35% by weight and the phosphorus oxide is present in an amount of about 1 to about 12% by weight. The oxides may be present as solid solutions or mixed oxides, or as mixtures of oxides.

One or more of $CaF_2$, $B_2O_3$, $Al_2O_3$, MgO and $K_2O$ may be included in the composition in addition to silicon, sodium, calcium and phosphorus oxides. The $B_2O_3$ may be present in an amount of up to 10% by weight, the $K_2O$ may be present in an amount of up to 8% by weight, the $Al_2O_3$ may be present in an amount of up to 4% by weight, the MgO may be present in an amount of up to 5% by weight and the $CaF_2$ may be present in an amount of up to about 30% by weight.

One example of particulate bioactive glass is Bioglass® 45S5 which has a composition including about 45% by weight silicon dioxide (SiO2), about 24.5% by weight sodium oxide (Na2O), about 6% phosphorus oxide (P2O5), and about 24.5% by weight calcium oxide (CaO) available from Schott Glass/US Biomaterials. Another example is known as Actysse BG, a particulate bioactive glass mixed with mica available from Engelhard Corporation, Iselin, N.J.

The bioactive glass of the present invention may be used in either particulate or extract form. Preferably, where particulate bioactive glass is used, particulate, non-interlinked bioactive glass is selected. This glass is in the form of small, discrete particles, rather than a fused matrix of particles or a mesh or fabric (woven or non-woven) of glass fibers. Under certain conditions, discrete particles of the bioactive glass may tend to cling together due to electrostatic or other forces, but these particles are still considered to be non-interlinked. Typically, the average particle size is about 90 microns or less. Preferably, the average particle size is less than about 20 microns, or, more preferably, less than about 5 microns, and even more preferably less than about 1 micron. Particle size, as used herein, is measured by SEM or other optical microscopy techniques, or by laser light scattering techniques (i.e. using a Coulter counter).

The bioactive glass may be prepared in any way known by those of ordinary skill in the art. For example, the bioactive glass may be provided as melt-derived glass, sol-gel derived glass or sintered glass particles. The sintered glass particles may be in sol-gel derived, or pre-reacted melt derived form. Melt derived glass typically is prepared by mixing grains of oxides or carbonates, melting and homogenizing the mixtures at high temperatures, generally about 1250 to about 1400° C. The molten glass can be fritted and milled to produce a small particulate material. Sol-gel derived glass is typically prepared by synthesizing an inorganic network by mixing metal alkoxides in solution, followed by hydrolysis, gelation, and low temperature (less than about 1000° C.) firing to produce glass.

The bioactive glass may also be used in extract form. An extract of bioactive glass is a solution of ions derived from bioactive glass. Typically, the solution of bioactive glass comprises ions and substantially no particles. Solutions also include suspensions and dispersions of bioactive glass. For example, an extract of bioactive glass may be formed from a solution made by reacting bioactive glass particles in an appropriate solvent such as water or tris buffer for an appropriate amount of time to create a solution of bioactive glass. The solution may then be filtered and used as a bioactive glass extract which is substantially particle free. The ratio of ions in solution will depend on the bioactive glass starting material and the amount of time it reacts in solution. The ion ratios may be controlled by use of various bioactive glass materials or by varying the reaction time.

The bioactive glass typically will be applied directly to hair in conjunction with a carrier. The carrier may be aqueous or nonaqueous. The carrier preferably will be aqueous, but may also be based on alcohol, other organic materials or combinations thereof. Alternatively, compositions can be provided in the form of aerosol sprays, foams or gels.

The bioactive glass component is typically employed in an amount of from about 0.5 to about 50% by weight, preferably from about 2 to about 30%, and more preferably from about 4 to about 10% by weight, based on the weight of the composition.

Slightly soluble metal hydroxides, including most divalent metal hydroxides, are not soluble enough in water to generate sufficient soluble hydroxide ions to effect relaxation of keratin fibers. This can be represented by the following, in which the equilibrium favors the left side of the reaction:

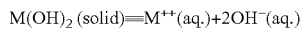

Therefore, in traditional relaxers containing slightly soluble metal hydroxides, the equilibrium was pushed to the right side and the reactions driven to completion by the precipitation of $M^{++}$ as an insoluble compound such, for example, as $CaCO_3$.

Novel methods such as those described and claimed in U.S. Pat. No. 6,562,327, the entire contents of which is hereby incorporated by reference, utilize a complexing agent to dissociate the multivalent metal hydroxide and chelate or sequester the $M^{++}$. The complexing agent and the multivalent metal form a complex that in most cases has a stronger interaction between the complexing agent and the metal. As a result, the complexing agent removes the metal from the above reaction medium and allows the equilibrium to be shifted to the right side.

The complexing agent may be a chelating agent or sequestering agent that leads to a partial or full dissociation of the at least one hydroxide generator. Regardless, the complexing agent chelates, sequesters or otherwise ties up the counter ion of the hydroxide, allowing more hydroxide ions to be liberated into solution. In other words, the net effect of the complexation is the generation of enough soluble hydroxide ions to effect relaxation/straightening of keratin fibers without relying on the precipitation of $M^{++}$ as $CaCO_3$.

The complexing agents of the present invention include, but are not limited to, any chelating agents or sequestering agents. A chelating agent is a compound or ligand that can bind to a metal ion, usually through more than one ligand atom, to form a chelate. See Lewis, R. J., Hawley's Condensed Chemical Dictionary p. 240 (1997). A chelate is usually a type of coordination compound in which a central metal ion such as $Co^{2+}$, $Ni^{2+}$, $Cu^{2+}$, $Ca^{2+}$ or $Zn^{2+}$ is attached by coordinate links to two or more nonmetal atoms, i.e., ligands, in the same molecule. Common chelating agents include ethylene-diaminetetraacetic acid (EDTA), nitrilotriacetic acid, and ethyleneglycol-bis(β-amino-ethyl ether)-N,N-tetraacetic acid.

Sequestering agents may be any material which prevents an ion from exhibiting its usual properties due to close combination with that material. Id. at 991. Certain phosphates, for example, form a coordination complex with metallic ions in solution so that the usual precipitation reactions are prevented and calcium soap precipitates are not produced from hard water treated with certain phosphates and metaphosphates. Id. Other examples of sequestering agents include hydroxy carboxylic acids such as gluconic, citric and tartaric acids. Id.

Examples of complexing agents that may be useful in the practice of the invention include, but are not limited to, organic acids and salts thereof. The salts of the organic acids of the present invention may contain an organic or inorganic cation. In a preferred embodiment, the complexing agent is chosen from mono-, di-, or poly-, amino- and hydroxy-carboxylic acids, mono-, di-, or poly-, amino- and hydroxy-sulfonic acids, and mono-, di-, or poly-, amino- and hydroxy-phosphonic acids.

In a further preferred embodiment, the complexing agent is chosen from ethylene diamine tetraacetic acid (EDTA) and its salts; N-(hydroxyethyl)ethylene diamine triacetic acid and its salts; aminotrimethylene phosphonic acid and its salts; diethylenetriamine-pentaacetatic acid and its salts; lauroyl ethylene diamine triacetic acid and its salts; nitrilotriacetic acid and its salts; iminodisuccinic acid and its salts; tartaric acid and its salts; citric acid and its salts; and N-2-hydroxyethyliminodiacetic acid and its salts. The salts may be chosen from salts with organic or inorganic cations. In one embodiment, the inorganic cation is chosen from potassium, sodium or lithium.

The complexing agent may also be chosen from a phosphate or silicate that demonstrates chelating or sequestering properties such as tripotassium or trisodium phosphate, or disodium or dipotassium silicate; an amino acid; or a crown ether. In one embodiment, an amino acid such as monosodium glutamate, which is a known calcium chelator, is used as a complexing agent.

In a further preferred embodiment, a salt of EDTA, such as sodium, lithium, potassium or guanidine EDTA, is employed as the complexing agent. EDTA has a strong calcium binding constant over a wide range of pH. For example, tetrasodium EDTA solubilizes calcium hydroxide in aqueous media to give a clear solution. The use of a complexing agent, such as tetrasodium EDTA that solubilizes the metal ion of a multivalent metal hydroxide offers the benefits of no "ashing". However, the use of complexing agents that do not completely solubilize the metal ion and only form slightly soluble or sparingly soluble complexing agent-metal ion complexes is also within the practice of the invention.

In another embodiment, the complexing agent may be a "soft" base or cation, e.g., organic cations such as guanidine, mono-, di- or tri-ethanolamine, and other amines, and a chelating or sequestering anion. A combination of a "soft" base or cation and a chelating or sequestering anion may be effective if the "soft" cation exists at a high enough pH to achieve straightening. For example, amino acids such as arginine may be used to neutralize EDTA to make a "soft base"/strong chelator pair.

Other examples of complexing agents which may be used include, but are not limited to, α-amino carboxylic acids and their derivatives, α-hydroxy carboxylic acids and their derivatives, α-thio carboxylic acids and their derivatives, α-hydroxy thioacids and their derivatives, mucic acid and its derivatives, and combinations thereof.

The present invention also provides for a simple screening test to determine the applicability of a complexing agent for use in the compositions of the present invention. By titrating a suspension of a multivalent metal hydroxide, such as $Ca(OH)_2$, with the complexing agent of interest, the chelating or sequestering properties may be observed. If the solution reaches a pH sufficient for relaxing/straightening keratin fibers, then the complexing agent is a good candidate for use in the compositions of the present invention. As was noted previously, the pH for effectuating relaxation/straightening of keratin fibers is typically at least about 11, preferably at least about 12, and more preferably at least about 13.

In a further preferred embodiment, the complexing agents of the present invention offer one or more of the following benefits: compatibility with keratin conditioning ingredients (polyquats, polymers, proteins, alkylquaternary ammonia compounds, silicones, etc); a stable mixture of complexing agent and multivalent metal hydroxide that can be stored for later use, an advantage which is not possible with compositions that result in the unstable guanidinium hydroxide; and the absence of a precipitation by-product and/or the absence of the need to apply a decalcifying shampoo after relaxing.

The complexing agent is employed in an amount of up to about 75% by weight, preferably from about 2 to about 50% by weight, and more preferably from about 5 to about 30% by weight, based on the weight of the composition.

Mixtures of complexing agents including mixtures of at least one chelating agent and at least one sequestering agent are also within the practice of the invention. In one embodiment, a less active chelating agent such as pentasodium aminotrimethylene phosphonate, may be mixed with a more active chelating agent, such as EDTA, to achieve the desired relaxing/straightening of keratin fibers at a slower rate.

Regardless of which type of hydroxide generator is used (soluble monovalent hydroxide for which a complexing agent is not necessary or slightly soluble multivalent metal hydroxide which requires the presence of a complexing agent), due to the alkalinity associated with the system, skin irritation is a constant problem.

The composition of the present invention may be sold as either a single composition in a powder system or as a multi-component kit for relaxing/straightening keratin fibers which comprises at least two separate components. In the case of a multi-component kit, a first component of the kit contains the hydroxide generator which may be present in the form of an emulsion, solution, suspension, gel or paste. A second component of the kit contains an activating composition comprising the bioactive glass component by itself, or in combination with a complexing agent or mixture of complexing agents in order to dissociate the at least one hydroxide generator in sufficient quantity to effect relaxation/straightening of keratin fibers. This second component may also be in the form of an emulsion, suspension, solution, gel or paste. The skilled artisan, based on the stability of the composition and the application envisaged, will be able to determine how the compositions should be stored and mixed.

In a preferred embodiment, one of the components of a multicomponent kit will contain enough water or other ionizing solvent to ensure that, upon mixing, enough of the generated hydroxide ions remain in solution to effect relaxation/straightening of keratin fibers.

The compositions of the present invention may also include ion exchange resins such as silicates. In one embodiment the silicate is a zeolite and more preferably a zeolite clay. The ion exchange resins may increase relaxing efficiency or enable the skilled artisan to control the rate of generation of soluble hydroxides.

Not to be limited as to theory, it is believed that the ion exchange resin participates in the relaxing/straightening process through an ion exchange mechanism. The ion exchange reversible reaction, which is the interchange of the multivalent metal ions from the multivalent metal hydroxide to the ion exchange resin, releases hydroxide at a much slower rate than does the complexing agent. Thus, the ion exchange resin can be used in combination with a complexing agent to modulate or control the rate of release of the soluble hydroxide, producing a mixed composition for more gentle or partial relaxing.

Any ion exchange resin which is effective in participating in the relaxing/straightening process is within the practice of the invention, including, but not limited to, silicates of aluminum and an alkali metal such as sodium, lithium, potassium or combinations thereof including analcime, chabazite, gmelinite, harmotome, levynite, mordenite, epistilbite, heulandite, natrolite, stilbite, edingtonite, mesolite, scolecite, thomosonite, brewsterite, faujasite, gismondine, laumontite, phillipsite, and aluminosilicate.

The present invention is also drawn to a process for relaxing/straightening keratin fibers. The process of the present invention involves generating hydroxide ions in an ionizing solvent by adding an activating composition to at least one hydroxide generator. The activating composition comprises a bioactive glass and, optionally, a complexing agent or a mixture of complexing agents effective for dissociating the hydroxide generator in sufficient quantity to effect relaxing/straightening of the keratin fibers. A composition containing the generated hydroxide ions is formed and the composition is applied to keratin fibers for a period of time to relax/straighten the keratin fibers. The composition is removed from the fibers when the desired level of relaxation of the keratin fibers has been reached.

The ionizing solvent is preferably a solvent that lowers the ionic bonding forces in the solute molecules enough to cause separation of their constituent atoms. In a further preferred embodiment the ionizing solvent is chosen from water and dimethyl sulfoxide (DMSO).

The method also encompasses forming the hydroxide ions in situ, i.e., while on the keratin fibers, by mixing at least one hydroxide generator and the bioactive glass component and, optionally the complexing agent in the presence of the keratin fibers.

The invention will be illustrated by, but is not intended to be limited to, the following examples.

EXAMPLE 1

Complexing of Solid $Ca(OH)_2$ with $Na_4EDTA$

A screening test to determine the applicability of a complexing agent for use in the compositions of the present invention was carried out. A solution of the complexing agent, 3 g of Versene 220 (tetrasodium EDTA ($Na_4EDTA$), 0.0066 moles) in 97 g of water, was titrated with the multivalent metal hydroxide solid, $Ca(OH)_2$. At the end of the reaction, 0.60 g of $Ca(OH)_2$ had been dissolved in the solution. Since the known solubility of $Ca(OH)_2$ is 0.15 g/100 ml of water, the amount of $Ca(OH)_2$ further dissolved in the solution due to the chelation of $Na_4EDTA$ was 0.45 g or 0.0061 mole. The results are shown in Table 1.

Tetrasodium EDTA has a strong calcium binding constant in the high alkaline range. The results demonstrated that the complexing process occurs up to a 1:1 molar ratio of the complexing agent:metal hydroxide. The result was the total chelation of $Ca(OH)_2$ by $Na_4EDTA$ at 1:1 molar ratio and the release of hydroxide ions to the solution. Since the solution reached a pH sufficient for relaxing/straightening keratin fibers, tetrasodium EDTA is a good candidate for use as a complexing agent of the present invention. In addition, the EDTA may be a preferred complexing agent since the EDTA-Ca chelation complex remains soluble in the reaction medium.

TABLE 1

$Ca(OH)_2$ Solubilized by EDTA

| g $Ca(OH)_2$ added | pH | Appearance |
|---|---|---|
| 0 | 11.62 | Clear |
| 0.20 | 13.23 | Clear |

TABLE 1-continued

Ca(OH)$_2$ Solubilized by EDTA

| g Ca(OH)$_2$ added | pH | Appearance |
|---|---|---|
| 0.40 | 13.52 | Clear |
| 0.60 | 13.59 | Clear |
| 0.65 | 13.63 | Cloudy |

EXAMPLE 2

Relaxing Efficiency of the Relaxers: Procedure for Measuring Relaxing Efficiency A solution of tetrasodium EDTA was added to a calcium hydroxide cream. After mixing for 3 minutes, the mixture was applied to a natural kinky hair swatch that was stretched and taped in a straight configuration. The relaxer mixture was worked into the hair swatch for 5 minutes and the treated hair swatch was allowed to stand at ambient temperature for another 15 minutes. The hair swatch was rinsed and shampooed then placed in the humidity chamber at 90% Relative Humidity for 24 hours. The % Relaxing Efficiency (% RE) is defined as:

% $RE = (Lf/Lt) \times 100$ where Lf=Length of the relaxed hair after 24 hours at 90% RH
$L_t$=Length of the hair at the straight configuration.

Relaxing Efficiency of A Hair Relaxer with an EDTA Complexing Agent

The effect of a Na4EDTA/Ca(OH)2 mixture on relaxing hair was studied. A Ca(OH)2 cream having the following formula was prepared:

| Material | % w/w |
|---|---|
| Cetyl alcohol | 1.0 |
| Steareth-2 | 0.5 |
| Steareth-10 | 2.5 |
| Mineral Oil | 15.0 |
| Petrolatum | 5.5 |
| Cetearyl alcohol and Cetearyl Phosphate | 7.5 |
| Propylene Glycol | 3.0 |
| Calcium Hydroxide | 5.0 |
| Water | 60.0 |

Mixtures of 6.3 g of the Ca(OH)$_2$ cream (0.315 g or 0.00425 moles of calcium hydroxide) and one of the Na$_4$EDTA solutions having the concentrations shown in Table 2 were stirred for 2 minutes. The resulting composition was applied to heat treated kinky hair with combing for 5 minutes and allowed to stand for an additional 15 minutes at room temperature. The treated hair was rinsed with water and shampooed with sodium laureth sulfate (SLES). The relaxing efficiency for each activating composition in Table 2 is shown.

While tetrasodium EDTA alone or the cream without activator does not relax the hair in 20 minutes, the addition of the traditional activator of 1.8 g of 25% guanidine carbonate produces 93% relaxation (A, B, C). When the guanidine salt was replaced with tetrasodium EDTA, relaxation increased in proportion to the added EDTA (D, E, F). Not to be limited as to theory, this appears to be because the chelation of one EDTA per Ca$^{++}$ releases two soluble hydroxides. Therefore, when measured by "straightness," not as much EDTA is required. Even reducing the moles of Ca(OH)$_2$ and Na$_4$EDTA by half (J), while still maintaining a 0.5/1.0 EDTA/Ca(OH)$_2$ molar ratio, resulted in efficient hair relaxing. Higher amounts of EDTA provided relaxation at different efficiencies (G, H, I).

TABLE 2

Relaxing Efficiency

| | g & moles of Ca(OH)$_2$ | Activator | Moles Na$_4$EDTA | Relaxing Efficiency (% RE) |
|---|---|---|---|---|
| A | 0.315 g, 0.00425 moles | 1.8 g water | 0 | 33% |
| B | None | 1 g Na$_4$EDTA/1.8 g water | 0.00221 | 35% |
| C | 0.315 g, 0.00425 moles | 1.8 g of 25% Guanidine Carbonate | — | 93% |
| D | 0.315 g, 0.00425 moles | 0.2 g Na$_4$EDTA/1.8 g water | 0.00044 | 60% |
| E | 0.315 g, 0.00425 moles | 0.4 g Na$_4$EDTA/1.8 g water | 0.00088 | 77% |
| F | 0.315 g, 0.00425 moles | 0.7 g Na$_4$EDTA/1.8 g water | 0.00155 | 93% |
| G | 0.315 g, 0.00425 moles | 1 g Na$_4$EDTA/1.8 g water | 0.00221 | 87% |
| H | 0.315 g, 0.00425 moles | 1.5 g Na$_4$EDTA/2 g water | 0.00331 | 86% |
| I | 0.315 g, 0.00425 moles | 3 g Na$_4$EDTA/3 g water | 0.0062 | 76% |
| J | 0.15 g, 0.00202 moles | 0.5 g Na$_4$EDTA/0.9 g water | 0.0011 | 90% |

EXAMPLE 3

The Complexation Reaction of Various Chelating Agents

A total of 2 g of the chelating agent indicated below in Table 3 was added slowly, with stirring, to a slurry of 5% Ca(OH)$_2$. A steady increase in the pH of the solution was observed upon the addition of the chelating agent. Table 3 shows the initial pH of the calcium hydroxide slurry and the final pH of the solution after addition of the chelating agent. The increase in pH of the solution demonstrated that the chelating agents chelate the calcium ions, allowing the insoluble calcium hydroxide to dissociate and release hydroxide ions into the solution.

TABLE 3

Chelation of Ca(OH)$_2$

| Activator | Initial pH of Ca(OH)$_2$ slurry | Final pH of Ca(OH)$_2$ solution |
|---|---|---|
| Tetrasodium EDTA[1] | 13.01 | 13.66 |
| Trisodium HEDTA[2] | 12.96 | 13.68 |
| Pentasodium Aminotrimethylene Phosphonate[3] | 13.05 | 13.49 |
| Potassium Tartrate | 13.05 | 13.52 |
| Sodium Citrate | 13.02 | 13.49 |
| Tripotassium Phosphate | 13.02 | 13.30 |
| Sodium Metasilicate[4] | 13.00 | 13.52 |

[1]Tetrasodium Ethylene diamine tetraacetate
[2]Trisodium n-[hydroxyethyl]-ethylene diamine triacetate
[3]Pentasodium [nitrilotris(methylene)]-tris-phosphonate
[4]Disodium silicate

EXAMPLE 4

The Effectiveness of Calcium Hydroxide and Complexing Agents as Hair Relaxers Natural kinky hair was relaxed using the above 5% calcium hydroxide cream and various complexing agents shown in Table 4. All of the mixtures had a 1:1 molar ratio of the Ca(OH)2:complexing agent. The results demonstrated that common chelators, such as carboxylates, phosphates, and phosphonates are efficient complexing agents.

TABLE 4

Relaxing Efficiency of Various Complexing Agents

| Complexing Agent | Relaxing Efficiency, % |
| --- | --- |
| Trisodium HEDTA[1] | 95 |
| Pentasodium DTPA[2] | 96 |
| Pentasodium Aminotrimethylene Phosphonate | 90 |
| Dipotassium Tartrate | 91 |
| Sodium Citrate | 89 |
| Tripotassium Phosphate | 90 |
| LED3A[3] | 92 |

[1]Trisodium n-[hydroxyethyl]-ethylene diamine triacetate
[2]Pentasodium diethylene triamine-pentaacetate
[3]Trisodium Lauroyl ethylene diamine triacetate

EXAMPLE 5

Complexation of Divalent Metal Hydroxides to Generate Hydroxide Ions

An equimolar amount of an insoluble divalent metal hydroxide was added to a solution of a complexing agent. The change in pH and the visual appearance of the mixture were observed. The results in Table 5 show that the pH of the solution increased upon the addition of the divalent metal hydroxide. In all but one case, the solution remained clear or turned clear after an extended amount of time. The increase in the pH and the clarity of the solution confirm the complexation of the divalent metal ions and the liberation of the hydroxide ions into the solution.

TABLE 5

Chelation of Different Divalent Metal Hydroxides

| Complexing Agent | pH | Divalent Metal Hydroxide | pH* | pH of 1:1 molar mixture | Appearance |
| --- | --- | --- | --- | --- | --- |
| Trisodium HEDTA | 12.58 | Ca(OH)$_2$ | 12.4 | 13.17 | Clear |
| Pentasodium DTPA | 11.52 | Mg(OH)$_2$ | 10.80 | 13.02 | Cloudy |
| Tetrasodium EDTA | 11.52 | Cu(OH)$_2$ | 8.38 | 12.72 | Clear |
| Tetrasodium EDTA | 11.52 | Sr(OH)$_2$ | 13.01 | 13.38 | Clear |
| Trisodium HEDTA | 12.60 | Co(OH)$_2$ | 10.63 | 13.38 | Clear |

*pH of the divalent metal hydroxide slurry

EXAMPLE 6

Strontium Hydroxide/Chelator as a Hair Relaxer

A strontium hydroxide relaxer gel was prepared according to the following formula:

| Material | % w/w |
| --- | --- |
| Mineral Oil | 15.0 |
| Petrolatum | 5.5 |
| Strontium Hydroxide Octahydrate | 18.6 |
| Propylene Glycol | 3.0 |
| Acrylates/Ceteth-20 Itaconate Copolymer | 7.0 |
| Water | 50.9 |

Six grams of the relaxer gel were mixed with a solution of 1.83 g tetrasodium EDTA in 2 g of water and the mixture was applied to kinky hair. The relaxing efficiency of the strontium hydroxide/EDTA hair relaxer was found to be in excess of 95%.

EXAMPLE 7

The Effects of Calcium Hydroxide Concentrations

A series of relaxer creams having a calcium hydroxide concentration ranging from 2% to 10% was prepared. For example, a typical 5% Ca(OH)$_2$ cream was formulated as follows:

| Materials | % w/w |
| --- | --- |
| Cetyl alcohol | 1.0 |
| Steareth-2 | 0.5 |
| Steareth-10 | 2.5 |
| Mineral Oil | 15.0 |
| Petrolatum | 5.5 |
| Cetearyl alcohol and Cetearyl Phosphate | 7.5 |
| Propylene Glycol | 3.0 |
| Calcium Hydroxide | 5.0 |
| Water | 60.0 |

A solution of 1.83 g of tetrasodium EDTA was added to 6 g of each of the relaxer creams and the resulting composition was applied to strands of natural kinky hair as described above. As a comparative test, the hair was also relaxed using a commercial no-lye relaxer (Optimum Care® from Soft Sheen®) and a commercial lye relaxer (Hair Werk from Soft Sheen®). The relaxing efficiency for each composition is shown in Table 6.

TABLE 6

Comparison of Relaxer Creams

| Relaxer Cream | Complexing Agent:Metal Hydroxide Molar Ratio | % Relaxing Efficiency |
| --- | --- | --- |
| Optimum Care ® | — | 99 |
| Hair Werk | — | 98 |
| 10% Ca(OH)$_2$ | 2:1 | 98 |
| 7% Ca(OH)$_2$ | 1.4:1 | 98 |
| 5% Ca(OH)$_2$ | 1:1 | 79 |
| 4% Ca(OH)$_2$ | 0.8:1 | 80 |
| 2% Ca(OH)$_2$ | 0.4:1 | 53 |

The results indicate that natural kinky hair was relaxed by the mixture of tetrasodium EDTA and the cream containing various concentrations of the calcium hydroxide. One should note that a low relaxing efficiency does not necessarily indicate a negative result. A lower relaxing efficiency may be intended by the skilled artisan depending on the amount of straightening desired and the application envisaged.

EXAMPLE 8

The Effects of Complexing Agent Concentrations

A solution containing the percentage of tetrasodium EDTA shown in Table 7 was added to 6 g of the 7% $Ca(OH)_2$ cream of Example 7 and applied to natural kinky hair as described above. The results indicate that natural kinky hair was relaxed by the mixture of the $Ca(OH)_2$ cream and the solution containing tetrasodium EDTA and that above a certain ratio of tetrasodium EDTA:$Ca(OH)_2$ a lower relaxing efficiency is obtained.

TABLE 7

Effects of Varying Complexing Agent Concentrations

| g of $NA_4EDTA$ in 4 g of Water | Concentration of EDTA Solution (% w/w) | Complexing Agent: Metal Hydroxide Molar Ratio | % Relaxing Efficiency |
| --- | --- | --- | --- |
| 0.77 | 19 | 0.3:1 | 40 |
| 1.28 | 32 | 0.5:1 | 70 |
| 1.79 | 44 | 0.7:1 | 85 |
| 2.56 | 64 | 1:1 | 66 |
| 3.07 | 76 | 1.2:1 | 62 |
| 3.84 | 96 | 1.5:1 | 56 |

EXAMPLE 9

Use of the Complexing Agent in a Cream Composition

A two component hair relaxing composition was prepared. The first component, a cream composition containing the complexing agent tetrasodium EDTA, was prepared as follows:

| Materials | % w/w |
| --- | --- |
| Cetyl alcohol | 1.0 |
| Steareth-2 | 0.5 |
| Steareth-10 | 2.5 |
| Mineral Oil | 15.0 |
| Petrolatum | 5.5 |
| Cetearyl alcohol and Cetearyl Phosphate | 7.5 |
| Propylene Glycol | 3.0 |
| Tetrasodium EDTA | 30.5 |
| Water | 34.5 |

The second component was a solution containing $Ca(OH)_2$. The amount of $Ca(OH)_2$ in each of the second components tested is shown in Table 8. Six g of the first component was added to the second component, the resulting composition was mixed and applied to natural kinky hair. The relaxing efficiency for each composition is shown in Table 8.

TABLE 8

$Ca(OH)_2$ Solution Added to the Complexing Agent Cream

| Component 1: Complexing Agent Cream:Metal Hydroxide Molar Ratio | Component 2: g of Calcium Hydroxide in 2 g of Water | % Relaxing Efficiency |
| --- | --- | --- |
| 1.5:1 | 0.2 | 72 |
| 1:1 | 0.3 | 88 |
| 0.75:1 | 0.4 | 93 |
| 0.6:1 | 0.5 | 80 |

The results indicate that natural kinky hair was relaxed by the mixture in which a cream containing the complexing agent was added to a solution containing various amounts of calcium hydroxide.

A similar experiment was conducted where the $Ca(OH)_2$ solution component was added to the complexing agent cream component. Solutions of varying amounts of calcium hydroxide, as shown in Table 9, were added to 6 g of the above complexing agent cream. The relaxing efficiency of the resulting composition, when applied to naturally kinky hair, is shown below.

TABLE 9

Relaxing Efficiency of Two Component Hair Relaxers

| Component 1: g of Calcium Hydroxide in 2 g of Water | Component 2: Complexing Agent Cream: Metal Hydroxide Molar Ratio | % Relaxing Efficiency |
| --- | --- | --- |
| 0.3 | 1:1 | 93 |
| 0.2 | 1.5:1 | 86 |
| 0.1 | 3:1 | 44 |

The results indicate that natural kinky hair was relaxed by a multicomponent system in which a $Ca(OH)_2$ solution is added to a cream containing the complexing agent. These results establish the utility of the "reverse" addition sequence (metal hydroxide to the complexing agent) and the appropriate molar ratio.

Table 10 shows the results of varying the amount of complexing agent in the complexing cream described above. Component 1, a solution containing 0.3 g of $Ca(OH)_2$ in 2 g of water, was added to each of the different second components shown in Table 10. The hair relaxing efficiency of each two component composition is shown below:

TABLE 10

Relaxing Efficiency of Two Component Hair Relaxers

| Component 1: g of Calcium Hydroxide in 2 g of Water | Component 2: Complexing Agent Cream:Metal Hydroxide Molar Ratio | % Relaxing Efficiency |
| --- | --- | --- |
| 1.8 | 0.3:1 | 69 |
| 3 | 0.5:1 | 86 |
| 4.2 | 0.7:1 | 92 |
| 6 | 1:1 | 90 |
| 7.8 | 1.3:1 | 87 |

EXAMPLE 10

Addition of Zeolite Clay to Hair Relaxing Compositions

A solution of 0.3 g Ca(OH)$_2$ containing various amounts of Zeolite clay (Sodium Aluminosilicate from The PQ Corporation P.O. Box 840, Valley Forge, Pa. 19482) in 2 g of water was added to 1.8 g of the complexing agent cream of Example 9. The relaxing efficiency is shown in Table 11.

The results indicate that the addition of Zeolite clay to the hair relaxing composition improved the composition's relaxing efficiency.

TABLE 11

Effects of Adding Zeolite Clay to Hair Relaxing Compositions

| g of Zeolite Clay | % Relaxing Efficiency |
|---|---|
| 0 | 64 |
| 0.2 | 71 |
| 0.5 | 79 |
| 1 | 79 |

EXAMPLE 11

Trisodium Nitrilotriacetate as a Complexing Agent

Using the procedures described above, natural kinky hair swatches were relaxed using 6 g of the 6% Ca(OH)$_2$ cream and various activating compositions containing trisodium nitrilotriacetate (Trilon® A92 from BASF Corporation, Mt. Olive, N.J.) as the complexing agent. The results are shown in Table 12.

High relaxing efficiency was obtained over a wide range of complexing agent: metal hydroxide molar ratios. The data indicates that trisodium nitrilotriacetate is an efficient complexing agent for the hair relaxing process.

TABLE 12

Effect of Trisodium Nitrilotriacetate as an Activating Agent

| g Trisodium Nitrilotriacetate | Nitrilotriacetate:Ca(OH)$_2$ Molar Ratio | % Relaxing Efficiency |
|---|---|---|
| 1.5 | 1.2:1 | 90 |
| 1.25 | 1:1 | 90 |
| 0.87 | 0.7:1 | 94 |
| 0.75 | 0.6:1 | 96 |
| 0.63 | 0.5:1 | 98 |
| 0.5 | 0.4:1 | 98 |
| 0.375 | 0.3:1 | 60 |
| 0.25 | 0.2:1 | 55 |

EXAMPLE 12

The Effect of Trisodium Nitrilotriacetate in Various Concentrations of Calcium Hydroxide Natural kinky hair swatches were relaxed using 0.5 g of trisodium nitrilotriacetate and various creams that contained 3-6% Ca(OH)$_2$. The relaxing efficiency is shown in Table 13. The data demonstrates that trisodium nitrilotriacetate is an efficient complexing agent for hair relaxing compositions even at low concentrations of Ca(OH)$_2$.

TABLE 13

Trisodium Nitrilotriacetate at Various Concentrations of Ca(OH)$_2$

| % Ca(OH)$_2$ in the Cream | Trisodium Nitrilotriacetate:Ca(OH)$_2$ Molar Ratio | % Relaxing Efficiency |
|---|---|---|
| 6 | 0.40:1 | 98 |
| 5 | 0.48:1 | 98 |
| 4 | 0.60:1 | 97 |
| 3 | 0.80:1 | 95 |

EXAMPLE 13

Ability of Bioactive Glass to Generate Hydroxide

Solutions were made consisting of 8 grams of Calcium Hydroxide and 50 grams of deionized water and particulate bioactive glass Actysse BG at various amounts. The pH was measured. The results are shown in Table 14.

TABLE 14

Measured pH of Actysse BG/Calcium Hydroxide Solutions

| Amount of Actysse (in grams) | pH measured |
|---|---|
| 0 | 12.69 |
| 5 | 12.85 |
| 10 | 12.95 |
| 15 | 13.04 |
| 20 | 13.11 |
| 25 | 13.17 |
| 30 | 13.22 |
| 35 | 13.27 |

The result was that a gradual increase in pH was observed as the amount of Actysse BG increased in the solution, indicating that hydroxide ions were generated.

EXAMPLE 14

Ability of Bioactive Glass to Relax Hair

Solutions were made consisting of 0.4 grams of Calcium Hydroxide, Actysse BG at increments of 0, 1, 2, and 2.5 grams, and deionized water totaling 5 grams. Then the pH was measured. These solutions were applied to curly hair for 30 minutes and the % RE was determined. The results are shown in Table 15.

TABLE 15

Relaxing Efficiency of Curly Hair Treated with Actysse/Calcium Hydroxide Solutions

| Amount of Actysse BG (in grams) | Measured pH | % RE |
|---|---|---|
| 0 | 12.83 | 31 |
| 1 | 13.02 | 24 |
| 2 | 13.41 | 43 |
| 2.5 | 13.47 | 57 |

The results show that the relaxing efficiency (% RE) increased as the levels of Actysse increased.

EXAMPLE 15

"No Lye" (Guanidine Carbonate) Relaxer

A solution was made consisting of 0.28 grams of Calcium Hydroxide, 0.10 grams of Guanidine Carbonate, and deionized water totaling 5 grams. Another solution was made, similar to that of the first solution, except that Actysse BG was added at 2 grams and the amount of water was properly adjusted. Both solutions were applied to curly hair for 30 minutes and the % RE determined. The results are shown in Table 16.

TABLE 16

Relaxing Efficiency of Curly Hair Treated with "No Lye" Relaxers

| Solution | % RE |
|---|---|
| 0.28 g Ca(OH)$_2$<br>0.10 g Guanidine carbonate<br>4.62 g DI Water | 60% |
| 2.00 g Actysse BG<br>0.28 g Ca(OH)$_2$<br>0.10 g Guanidine carbonate<br>2.62 g DI Water | 76% |

The results show that the relaxing efficiency (% RE) increased when Actysse BG was added to a "no lye" relaxer.

EXAMPLE 16

"Lye" (Sodium Hydroxide) Relaxer

Solutions were made consisting of 1.3 grams of Calcium Hydroxide, 0.35 grams of Calcium Hydroxide, Actysse BG at increments of 0, 1, 2, 3, and 4 grams, and deionized water totaling 10 grams. The pH was measured, and these solutions were applied to curly hair for 30 minutes and the % RE determined. The results are shown in Table 17.

TABLE 17

Relaxing Efficiency of Curly Hair Treated with Lye Relaxers

| Solution | Measured pH | % RE |
|---|---|---|
| 0.00 g Actysse BG<br>1.3 g Ca(OH)$_2$<br>0.35 g NaOH (50% conc.)<br>8.35 g DI Water | 13.65 | 57% |
| 1.00 g Actysse BG<br>1.3 g Ca(OH)$_2$<br>0.35 g NaOH (50% conc.)<br>7.35 g DI Water | 13.76 | 67% |
| 2.00 g Actysse BG<br>1.3 g Ca(OH)$_2$<br>0.35 g NaOH (50% conc.)<br>6.35 g DI Water | 13.81 | 71% |
| 3.00 g Actysse BG<br>1.3 g Ca(OH)$_2$<br>0.35 g NaOH (50% conc.)<br>5.35 g DI Water | 13.90 | 89% |
| 4.00 g Actysse BG<br>1.3 g Ca(OH)$_2$<br>0.35 g NaOH (50% conc.)<br>4.35 g DI Water | 13.95 | 94% |

The results show that the relaxing efficiency (% RE) increased as the levels of Actysse/Calcium Hydroxide increased in a lye relaxer.

EXAMPLE 17

Relaxers using Chelating Agents

In this study, chelating agents, Potassium Citrate and Tetrasodium EDTA, were used to relax the hair.

Potassium Citrate Relaxer

A solution was made consisting of 0.36 grams of Calcium Hydroxide, 0.5 grams of Potassium Citrate, and 4 grams of DI Water. Another solution was made, similar to that of the first solution, except that Actysse BG was added at 4 grams. These solutions were applied to curly hair for 30 minutes and the % RE determined.

Tetrasodium EDTA Relaxer

One solution was made consisting of 0.36 grams of Calcium Hydroxide, 0.3 grams of Tetrasodium EDTA, and 2 grams of DI Water. Another solution was made, similar to that of the first solution, except that Actysse BG was added at 0.2 grams. These solutions were applied to curly hair for 30 minutes and the % RE determined.

The results are shown in Table 18.

TABLE 18

Relaxing Efficiency of Curly Hair Treated with Chelating Relaxers

| K$^+$ Citrate Relaxer | % RE | Na$_4$$^{++}$ EDTA Relaxer | % RE |
|---|---|---|---|
| 0.36 g Ca(OH)$_2$<br>0.50 g K$^+$ Citrate<br>4.00 g DI Water | 71% | 0.36 g Ca(OH)$_2$<br>0.30 g Na$_4$ EDTA<br>2.00 g DI Water | 81% |
| 4.00 g Actysse BG<br>0.36 g Ca(OH)$_2$<br>0.50 g K$^+$ Citrate<br>4.00 g DI Water | 76% | 0.20 g Actysse BG<br>0.36 g Ca(OH)$_2$<br>0.30 g Na$_4$ EDTA<br>2.00 g DI Water | 96% |

The results show that the addition of Actysse BG to both chelating relaxer formulas increases the relaxing efficiency.

EXAMPLE 18

Assessment of Irritation

The study objective is to assess irritation (burning, stinging, and itching) of panelists exposed to a lye relaxer containing Actysse BG compared to a lye relaxer without Actysse BG. Ten panelists, free of skin irritation and/or sunburn on the volar forearms, were treated in a randomized fashion with 0.02 g test product for 5 minutes. Panelists were asked to comment on any painful sensations, such as burning, stinging, and itching, for each test product. The following is an account of the test sample formulas:

Control Relaxer (pH 13.65)
13% Ca(OH)$_2$
1.75 % NaOH (50 W conc.)
85.25 % DI Water
Relaxer with 10 W Actysse (pH 13.76)
10% Actysse
13% Ca(OH)$_2$
1.75 % NaOH (50% conc.)
75.25 % DI Water The study results show that forty percent of panelists experienced more irritation (burning, stinging, and/or itching) from the control relaxer, while only twenty percent were more irritated from the relaxer containing Actysse BG.

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

What is claimed is:

1. A composition comprising:
    (a) at least one hydroxide generator in an amount sufficient to relax/straighten keratin fibers;
    (b) at least one bioactive glass component; and
    (c) at least one complexing agent,
    wherein the ratio of hydroxide generator to bioactive glass component is from about 0.09:1 to about 1.8:1,
    wherein the composition has a pH of 13 or greater.

2. The composition of claim 1 wherein the hydroxide generator is at least one monovalent metal hydroxide.

3. The composition of claim 2 wherein the hydroxide generator is present in an amount of from about 0.1 to about 3% by weight, based on the weight of the composition.

4. The composition of claim 1 wherein the hydroxide generator is at least one multivalent metal hydroxide.

5. The composition of claim 4 wherein the hydroxide generator is present in an amount of from about 0.1 to about 75% by weight, based on the weight of the composition.

6. The composition of claim 1 wherein the bioactive glass is present in an amount of from about 0.5 to about 50% by weight, based on the weight of the composition.

7. The composition of claim 1 wherein the complexing agent is present in the composition in an amount of from about 2 to about 50% by weight, based on the weight of the composition.

8. The composition of claim 1 wherein (b) is present in an amount of from about 4 to about 10% by weight and (c) is present in an amount of from about 5 to about 30% by weight, all weights based on the weight of the composition.

9. A multicomponent kit for relaxing/straightening keratin fibers comprising:
    (a) at least one compartment containing at least one hydroxide generator in an amount sufficient to relax/straighten keratin fibers; and
    (b) at least one compartment containing at least one bioactive glass component and at least one complexing agent,
    wherein the ratio of hydroxide generator to bioactive glass component is from about 0.09:1 to about 1.8:1,
    wherein when the contents of the two compartments are mixed, the resulting mixture has a pH of 13 or greater.

* * * * *